United States Patent [19]
Boussignac et al.

[11] Patent Number: 5,861,010
[45] Date of Patent: Jan. 19, 1999

[54] DEVICE FOR TEMPORARILY CLOSING A CANAL IN A BODY, IN PARTICULAR FOR ASSISTING THE FUNCTION OF THE HEART BY APPLICATION OF COUNTER-PRESSURE

[75] Inventors: Georges Boussignac, Antony; Pierre Hilaire, Paris, both of France

[73] Assignee: Laboratoires Nycomed S.A., France

[21] Appl. No.: 945,487

[22] PCT Filed: Apr. 22, 1996

[86] PCT No.: PCT/FR96/00608

§ 371 Date: Oct. 17, 1997

§ 102(e) Date: Oct. 17, 1997

[87] PCT Pub. No.: WO96/32971

PCT Pub. Date: Oct. 24, 1996

[30] Foreign Application Priority Data

Apr. 21, 1995 [FR] France .................................. 95 04794

[51] Int. Cl.⁶ ..................................................... A61M 1/12
[52] U.S. Cl. .................................. 607/18; 607/16; 604/96
[58] Field of Search ................................. 600/16–18, 31; 604/96; 606/194, 195, 192

[56] References Cited

U.S. PATENT DOCUMENTS

| | | | |
|---|---|---|---|
| 4,245,622 | 1/1981 | Hutchins, IV | 600/18 |
| 4,250,872 | 2/1981 | Tamari | 600/16 |
| 5,226,888 | 7/1993 | Arney | 606/194 |
| 5,318,532 | 6/1994 | Frassica . | |
| 5,342,305 | 8/1994 | Shonk | 606/194 |
| 5,360,403 | 11/1994 | Mische . | |
| 5,403,280 | 4/1995 | Wang | 606/194 |
| 5,558,642 | 9/1996 | Schweich, Jr. et al. | 606/194 |

FOREIGN PATENT DOCUMENTS

| | | |
|---|---|---|
| 0526102 | 2/1993 | European Pat. Off. . |
| 89 11307 | 11/1989 | WIPO . |
| 93 13826 | 7/1993 | WIPO . |

*Primary Examiner*—William E. Kamm
*Assistant Examiner*—Kennedy J. Schaetzle
*Attorney, Agent, or Firm*—Bierman, Muserlian and Lucas

[57] ABSTRACT

The present invention concerns a device for temporarily closing a canal in a body, in particular for assisting the function of the heart by application of counter-pressure. The device is characterised in that it comprises a first inflatable structure (1) which, in the inflated state, defines a sleeve shaped to match the internal surface of the canal, providing a central conduit (4). The device further comprises a second inflatable structure which expands radially, preferably from the exterior to the interior, is held by the first structure (1) and shaped such that, in the inflated state, it permits substantially complete closure of the central conduit (4) formed after inflation of the first structure. The device finally comprises means allowing each of these first and second inflatable structures to be in fluid communication with a fluid delivery source.

13 Claims, 4 Drawing Sheets

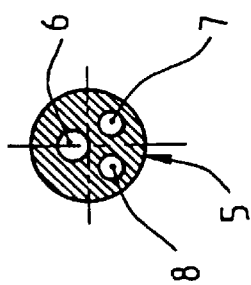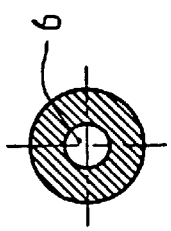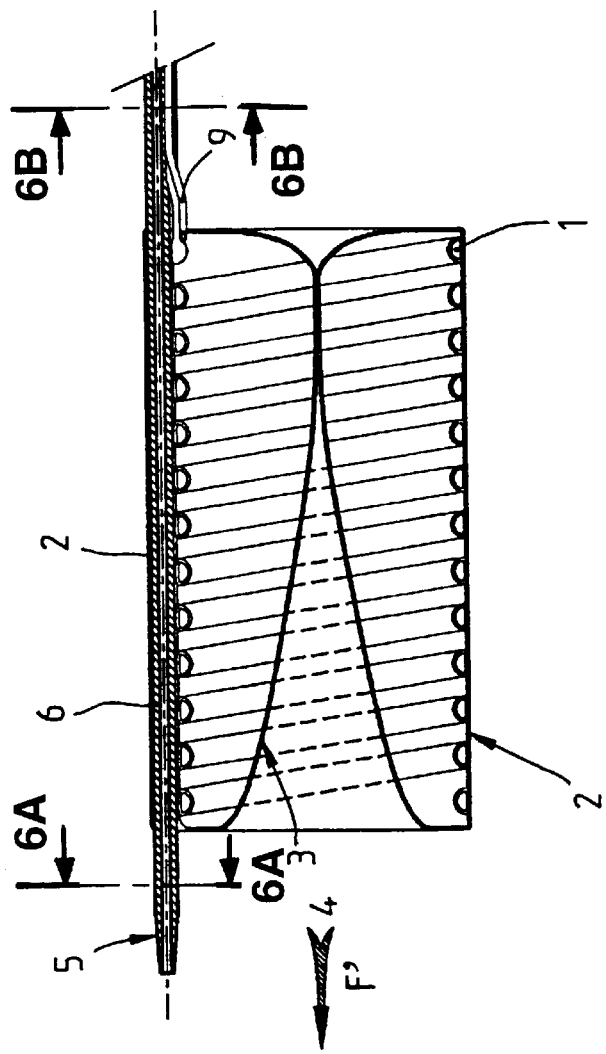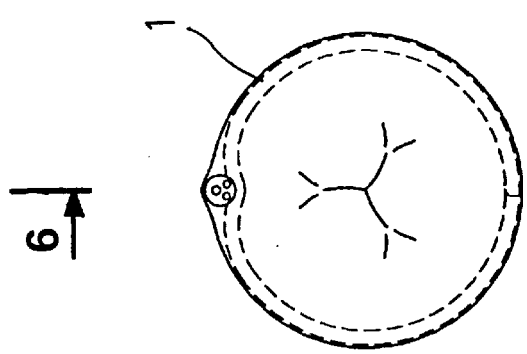

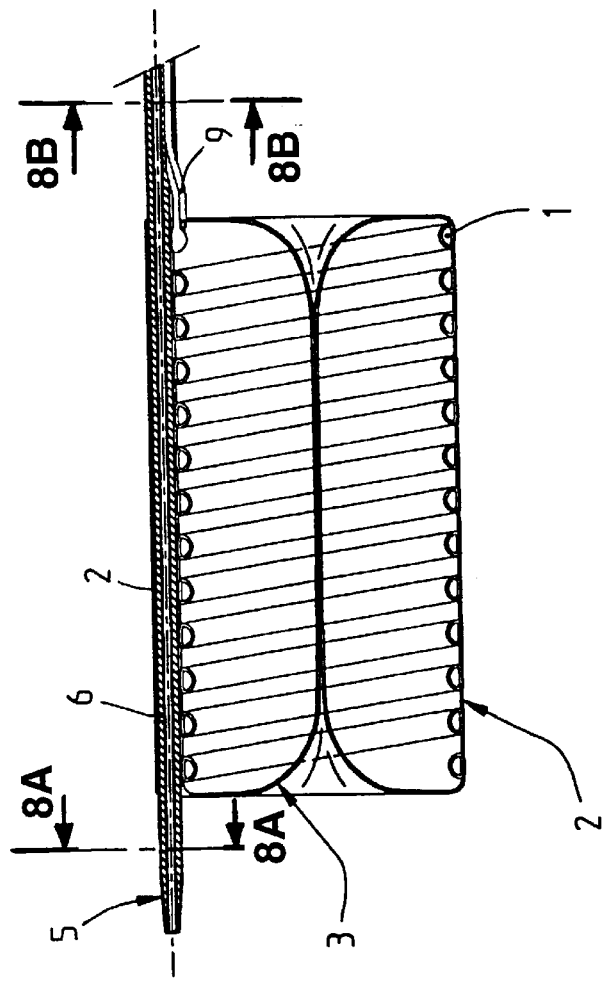
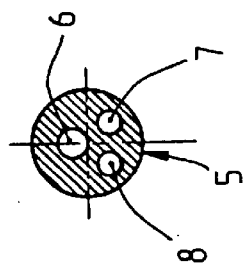
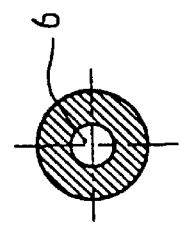
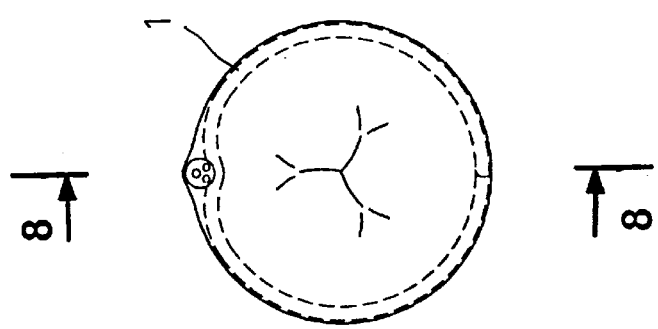

DEVICE FOR TEMPORARILY CLOSING A CANAL IN A BODY, IN PARTICULAR FOR ASSISTING THE FUNCTION OF THE HEART BY APPLICATION OF COUNTER-PRESSURE

The present invention relates in general terms to a device which is capable of being introduced inside a body canal in order to allow its temporary occlusion, preferably in a controlled manner.

The invention is applied mainly in the field of cardiac assistance by counter-pulsation in which this device is introduced into the aorta, and, for the sake of clarity, will be described below within the framework of this application.

It is obvious, however, that the invention must be considered as having a much broader scope which extends to any use requiring the optionally controlled occlusion of any body canal such as the esophagus, the trachea, the digestive tract or the urinary tract.

It is known that cardiac assistance by counter-pulsation is used principally in interventional cardiology in order to ensure irrigation of the brain during the treatment of coronary diseases.

This assistance is generally achieved with the aid of an elastic balloon catheter placed in the patient's aorta, which, when in the inflated state, obstructs this artery in a controlled manner in synchronisation with the heart pulsations.

This has the effect of blocking the blood flowing towards the lower parts of the body so that, during the systole, only the upper parts of the body, especially the heart and the brain, are preferentially supplied.

The catheters currently used to perform this technique generally consist of a tube containing a first channel, which allows the passage of a guide for facilitating the positioning of the balloon, and a second channel, the purpose of which is to allow the inflation and deflation of the balloon.

Synchronisation with the heart pulsations is achieved by means of a servo pump.

With each pulsation, the fully inflated balloon presses against the inner wall of the artery.

The repetition of these contacts between the balloon and the inner wall of the artery can be the cause of undesirable traumatisms.

Also, as the moving balloon also carries with it the various devices necessary for the intervention and thus presses them against the aortic wall with each pulsation, the above-mentioned risks of traumatisms are further increased.

Under these conditions, the main object of the present invention is to solve the technical problem consisting in the provision of a novel design of temporary occlusion device which, in particular, can be used easily and without traumatising the body canal.

The solution to this technical problem, according to the present invention, consists of a device for the temporary occlusion of a body canal containing a circulating fluid, which is useful especially for cardiac assistance by counter-pressure, characterised in that it comprises:

a first inflatable structure which, in the inflated state, defines a sleeve shaped so as to follow the internal surface of said canal, creating a central duct for the passage of said body fluid;

a second, radially expandable structure inflatable and deflatable independently of the first structure, held by said first structure and shaped so that, in the inflated state, it permits substantially total occlusion of said central duct formed after inflation of said first structure; and means of bringing each of said first and second inflatable structures into fluid communication with a source of fluid supply for the inflation and deflation of these structures.

Thus the novelty of the device according to the present invention lies mainly in the fact that the occlusion of the body canal is effected with practically no shock against the inner wall of the body canal.

Advantageously, the inflation of the above-mentioned second structure, causing the occlusion of said canal, is effected radially inwards from the outside, as distinct from the devices of the state of the art using a balloon which expands radially outwards from the inside.

This particular conformation of the second inflatable structure guarantees the total absence of shock against the inner wall of the body canal.

As indicated previously, the only effect of the balloon catheters used hitherto is to block the blood flowing towards the lower parts of the body. The assistance provided in this way can be defined as "passive".

On the basis of this observation, the inventors formulated and attempted to solve the novel technical problem consisting in the provision of a device capable of providing "active" assistance, resulting, within the framework of cardiac assistance by counter-pulsation, in the possibility of increasing the volume of blood ejected towards the brain by means of the occlusion device.

Thus, according to one particularly advantageous characteristic of the device according to the present invention, the above-mentioned second structure is shaped so that its inflation causes a displacement of the fluid contained in the above-mentioned central duct in the axial direction of the body canal.

As can be seen, within the framework of the application illustrated by way of example, such a conformation leads to a pumping system of the peristaltic type which, each time the aorta closes, ejects a volume of blood towards the brain which corresponds substantially to the volume of the second structure in the inflated state.

The assistance provided in this way can be qualified as active.

Of course, the peristalsis sought in the present application can easily be reversed within the framework of other applications.

Thus, within the framework of assistance of the peristaltic type, the occlusion of the central duct during inflation is initially effected at a point near the proximal end of said duct, and then propagates in the axial direction towards the distal end of said duct.

On the other hand, in the case where the peristalsis is reversed (assistance of the "anti-peristaltic" type), the propagation takes place in the opposite direction, i.e. from the distal end towards the proximal end of the central duct.

In one currently preferred embodiment, the above-mentioned first inflatable structure comprises a spiral-wound tube whose turns can be contiguous or, preferably, non-contiguous.

As a variant, this first structure can also be produced in the form of a double walled tube, for example as described in U.S. Pat. No. 5,108,370, which is incorporated here by way of reference.

The first inflatable structure of the device according to the present invention fulfils a dual function.

First of all, by coming into direct or indirect contact with the body canal, it protects the inner wall of said canal.

Furthermore, it makes it possible to hold the second inflatable structure while allowing expansion to take place radially inwards from the outside during inflation.

In one currently preferred embodiment, the above-mentioned second inflatable structure consists of a double walled tube.

As can be seen, it is the outer wall of this tube which is held by the first inflatable structure, the inner wall deforming during inflation until the above-mentioned central duct is substantially totally occluded.

According to one particularly advantageous characteristic, the spiral-wound tube forming the above-mentioned first inflatable structure is arranged between the two walls of the tube constituting the above-mentioned second inflatable structure.

As a variant, the double walled tube constituting the above-mentioned second inflatable structure can be arranged inside the first inflatable structure, being fixed thereto either directly, for example by gluing, or indirectly via any appropriate connecting means.

Advantageously, the occlusion device according to the present invention also comprises a catheter for inserting it inside the body canal.

This catheter will preferably have a radial and external arrangement relative to the above-mentioned first inflatable structure.

A further aim of the present patent application is to cover the use of a device for occluding a body canal, as defined above, for the manufacture of a device which helps to provide cardiac assistance by counter-pressure.

Other characteristics and advantages of the invention will also become apparent from the following description referring to the attached drawings, which are given solely by way of a non-limiting example and in which:

FIG. 5 is an end view, similar to FIG. 3, of a temporary occlusion device according to the present invention, shown in a use position during inflation of the second structure;

FIG. 6 is a cutaway view along the line 6—6 of FIG. 5;

FIG. 6A is a cutaway view along the line 6A—6A of FIG. 6;

FIG. 6B is a cutaway view along the line 6B—6B of FIG. 6;

FIG. 7 is an end view, similar to FIGS. 3 and 5, of a temporary occlusion device according to the present invention, shown in a use position after inflation of the above-mentioned first and second inflatable structures;

FIG. 8 is a cutaway view along the line 8—8 of FIG. 7;

FIG. 8A is a cutaway view along the line 8A—8A of FIG. 8; and

FIG. 8B is a cutaway view along the line 8B—8B of FIG. 8.

Figure 2B:
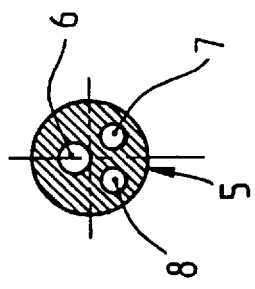
FIG. 2B is a cutaway view along the line 2B—2B of FIG. 2.
Figure 2A:
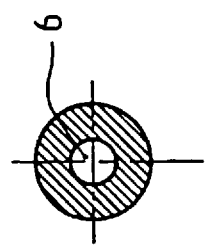
FIG. 2A is a cutaway view along the line 2A—2A of FIG. 2.
Figure 2:
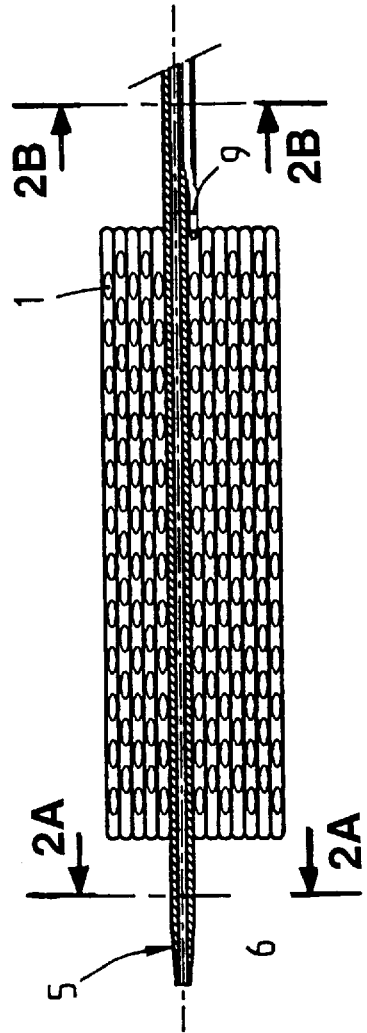
FIG. 2 is a cutaway view along the line 2—2 of FIG. 1.
Figure 1:
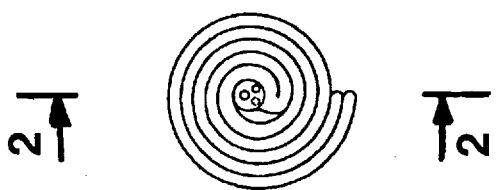
FIG. 1 is a schematic end view showing a device for the temporary occlusion of a body canal, according to the invention, before it is implanted.
Figure 4A:
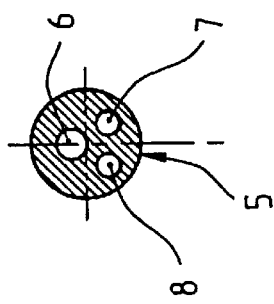
FIG. 4A is a cutaway view along the line 4A—4A of FIG. 4.
Figure 4B:
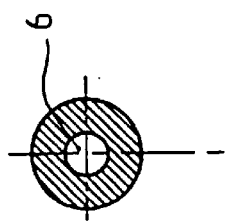
FIG. 4B is a cutaway view along the line 4B—4B of FIG. 4.
Figure 4:
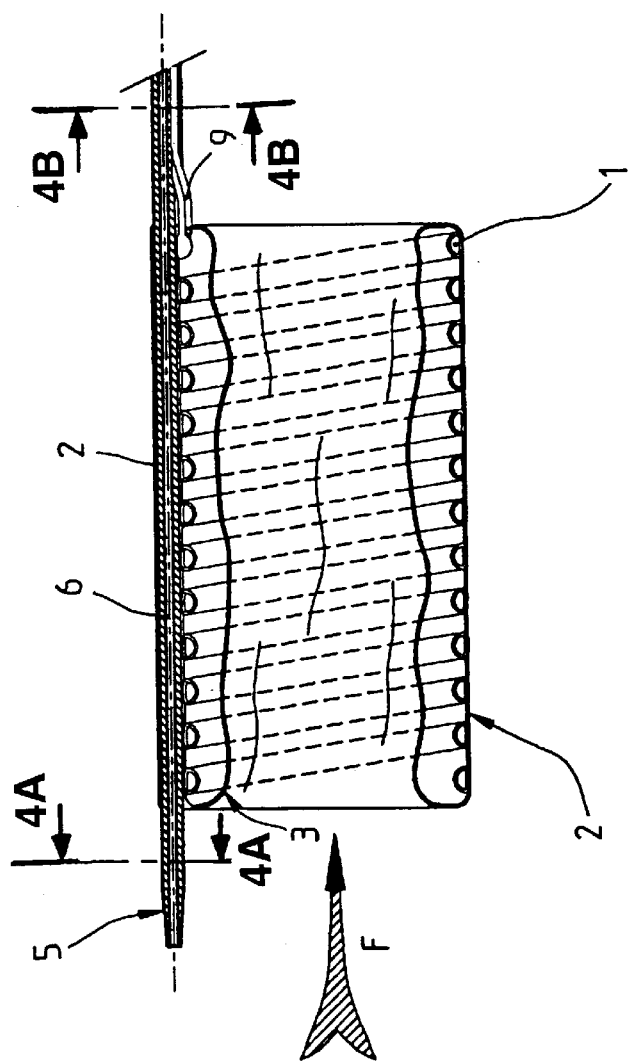
FIG. 4 is a cutaway view along the line 4—4 of FIG. 3.
Figure 3:
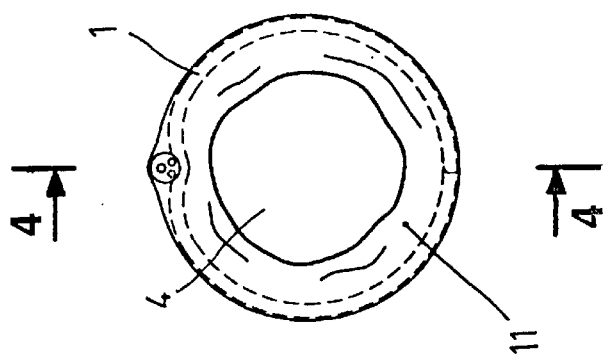
FIG. 3 is an end view, similar to FIG. 1, of a temporary occlusion device according to the present invention, shown in a use position in which only the first structure is in the inflated state.

FIGS. 1 to 8B therefore illustrate a currently preferred embodiment of a device for the temporary occlusion of a body canal, in its different positions:

prior to its implantation (FIGS. 1 to 2B);

in an implanted position in which only the first structure is in the inflated state, thereby allowing the body fluid to circulate (FIGS. 3 to 4B);

in a use position during inflation of the second structure so as to illustrate its operation in the "peristaltic" mode (FIGS. 5 to 6B); and in a use position at the end of inflation of the second inflatable structure, the latter substantially totally occluding the central duct of the first structure (FIGS. 7 to 8B).

In general terms, a device for the temporary occlusion of a body canal, according to the present invention, comprises two independently inflatable structures.

In the inflated state, the first inflatable structure defines a sleeve which is shaped so as to follow the internal surface of the body canal, creating a central duct 4.

This sleeve can be substantially cylindrical, as in the example shown, but can also be constructed with other shapes, for example a cone or a diabolo, in order to fit the anatomy of the implantation site.

In the example shown, this first structure consists of a spiral-wound tube 1 whose turns are not contiguous.

The tube 1 can be made for example of a material such as a semi-rigid thermoplastic, particularly a polyamide, a polyurethane or a copolymer of the PEBAX® type marketed by ATOCHEM.

In the example shown, the second inflatable structure consists of a double walled tube, namely a tube with an outer wall or membrane 2 and an elastic inner wall or membrane 3.

The outer membrane 2 is preferably arranged on the outside of the spiral-wound tube 1, being pressed by the latter (in the inflated state) against the inner wall of the body canal, which is not shown.

The elastic inner membrane 3 will preferably be made of a thermoplastic, which can be a polyamide, a polyurethane, a copolymer of the PEBAX® type or a silicone.

The same applies to the outer membrane 2, which will preferably be made of the same material as the inner membrane 3.

Advantageously, the length of the double channelled tube constituting the second inflatable structure is substantially equal to the length of the sleeve formed by the tube 1 in the inflated state.

As can be seen, the inflation of the above-mentioned double walled tube is accompanied by an inward radial expansion of its inner membrane 3, which will gradually cause the occlusion of the central duct 4.

To enable the device to operate in a manner similar to a peristaltic pump, it is necessary that, during the inflation of the second structure, the occlusion of the central duct 4 be initially effected, as shown in FIG. 6, at a point relatively near the proximal end of said duct and then propagate in the axial direction towards the distal end of said duct in order to reach the position shown in FIG. 8.

To achieve this objective, the thickness of the inner wall 3 of the double channelled tube forming the second inflatable structure will vary gradually from one end of the duct to the other, being smaller at the proximal end when operating in a peristaltic manner and larger at the proximal end when operating in an anti-peristaltic manner.

The occlusion device according to the present invention also comprises a catheter, designated in general terms by the reference number 5, the purpose of which is to enable said device to be implanted inside the body canal.

In a manner known per se, this catheter consists of a flexible elongate tube comprising a proximal part (not shown) and a distal part where the above-mentioned first and second inflatable structures are located.

The catheter 5 has a first lumen 6 extending over the whole of its length and allowing the passage of a guide wire (not shown).

The catheter 5 also comprises means for bringing each of said first and second inflatable structures into fluid communication with a source of fluid supply.

For this purpose, the catheter 5 has a second lumen 8 and a third lumen 7 extending substantially parallel to one another over the major part of its length and communicating respectively with the inflation chambers of the first and second inflatable structures, either via a radial hole made in the catheter wall or, preferably, via a flexible connector.

At the proximal end of the catheter 5, these second and third lumens are joined to a source of fluid supply, allowing the inflation and deflation of the first and second inflatable structures.

In a manner known per se, the proximal part of the catheter 5 will be equipped for this purpose with a three-way connector of the LUER LOCK type.

The fluid used for inflation will be for example a gas or a liquid under pressure.

In the drawings, the reference number 9 represents a flexible connector joining the third lumen 7 to the inflation chamber of the second inflatable structure.

In the currently preferred embodiment, the catheter 5 has a radial and external arrangement relative to the spiral-wound tube 1 constituting the first inflatable structure, along a generatrix of the sleeve formed by said tube in the inflated state.

More precisely, the catheter 5 is arranged between the outer membrane 2 of the second structure and the external surface formed by the tube 1.

As a variant, the catheter 5 can be arranged inside the spiral-wound tube 1, being joined directly or indirectly thereto.

The operation of the temporary occlusion device which has now been described can easily be deduced from its structure.

Thus the catheter 5, carrying the first and second inflatable structures in its distal part, is introduced with the aid of a metal guide, in conventional manner, as far as the chosen implantation site.

During this operation, the above-mentioned first and second inflatable structures have been folded, for example in a spiral as shown in FIGS. 1 to 2B, so that the dimensions of the catheter carrying these structures are smaller than the internal dimensions of the body canal into which the device is introduced.

The first inflatable structure is then inflated to form a sleeve which follows the internal surface of the canal, while at the same time creating an open central duct allowing the body fluid to circulate in the direction indicated by the arrow F in FIG. 4.

The second inflatable structure is then inflated in synchronisation with the heart pulsations by means of a conventional pump.

As the thickness of the inner wall 3 is smaller at the proximal end than at the distal end, the occlusion of the central duct resulting from the inflation of the second structure is initially effected at a point near the proximal end of the central duct 4 defined by the spiral-wound tube 1, as shown in FIG. 6.

When inflation continues, the occlusion thereby produced in the proximal part propagates in the axial direction towards the distal end of the central duct 4 to reach the position shown in FIG. 8.

The body fluid contained in the free space in the central duct 4 is thus driven back in the direction of the arrow F' shown in FIG. 6, permitting a peristaltic type of operation.

The body fluid ejected each time the canal closes makes the resulting assistance "active".

It should be noted that the device which has now been described can be provided with means for the easy removal of this device after intervention.

For this purpose, provision can be made for example for an elastic cylindrical sheath or a spiral-wound elastic thread arranged around the first and second inflatable structures so that the latter can fold and so that the catheter carrying these structures can easily be removed from the body canal into which it has been introduced.

The temporary occlusion device which has now been described is therefore particularly advantageous in comparison with the known devices of the state of the art, insofar as it makes it possible to provide active assistance without traumatising the body canal.

We claim:

1. Device for the temporary occlusion of a body canal containing a circulating fluid, comprising an inflatable structure which, in the inflated state, defines a sleeve shaped so as to follow the internal surface of said canal, creating a central duct for the passage of said body fluid, and means of bringing the inflatable structure into fluid communication with a source of fluid supply for the inflation and deflation of the structure, characterised in that it comprises:

a second, radially expandable structure inflatable and deflatable independently of the first structure, held by said first structure and shaped so that, in the inflated state, it permits substantially total occlusion of said central duct formed after inflation of said first structure; and means of bringing said second inflatable structure into fluid communication with a source of fluid supply for the inflation and deflation of this second structure.

2. Device according to claim 1, characterised in that the above-mentioned second inflatable structure can expand radially inwards from the outside.

3. Device according to claim 1, characterised in that the above-mentioned second inflatable structure is shaped so that its inflation causes a displacement of the fluid contained in the above-mentioned central duct (4) in the axial direction of the body canal.

4. Device according to claim 1, characterised in that the above-mentioned first inflatable structure comprises a spiral-wound tube (1).

5. Device according to claim 4, characterised in that the turns of the above-mentioned tube (1) are not contiguous.

6. Device according to claim 1, characterised in that the above-mentioned second inflatable structure consists of a double walled tube.

7. Device according to claim 6, characterised in that the above-mentioned spiral-wound tube (1) is arranged between the two walls (2, 3) of the tube constituting the above-mentioned second inflatable structure.

8. Device according to claim 1, characterised in that it also comprises a catheter (5) for inserting it inside the body canal.

9. Device according to claim 8, characterised in that the above-mentioned catheter (5) has a first lumen (6) extending over the whole of its length and allowing the passage of a guide wire.

10. Device according to claim 8, characterised in that the above-mentioned catheter (5) has a radial and external arrangement relative to the above-mentioned first inflatable structure.

11. Device according to claim 8, characterised in that the above-mentioned catheter (5) has a second lumen (8) extending over the major part of its length and communicating with the inflation chamber of the first inflatable structure, either via a radial hole made in the wall of said catheter or via a flexible connector, said lumen being joined at the proximal end of the catheter to a source of fluid supply for the inflation of said first structure.

12. Device according to claim 8, characterised in that the above-mentioned catheter (5) has a third lumen (7) extending over the major part of its length and communicating with the inflation chamber of the second inflatable structure, either via a radial hole made in the wall of said catheter or via a flexible connector (9), said lumen being joined at the proximal end of the catheter to a source of fluid supply for the inflation of said second structure.

13. Device which helps to provide cardiac assistance by counter-pressure, characterised in that it comprises a device for occluding a body canal, according to one of claim 1.

* * * * *